United States Patent [19]

Vora

[11] 4,341,911
[45] Jul. 27, 1982

[54] HYDROCARBON CONVERSION PROCESS FOR THE PRODUCTION OF GASOLINE

[75] Inventor: Bipin V. Vora, Elk Grove Village, Ill.

[73] Assignee: UOP Inc., Des Plaines, Ill.

[21] Appl. No.: 220,547

[22] Filed: Dec. 29, 1980

[51] Int. Cl.³ ............................................. C07C 2/58
[52] U.S. Cl. ................................... 585/332; 585/314; 585/331
[58] Field of Search ............... 585/314, 329, 330, 331, 585/332

[56] References Cited

U.S. PATENT DOCUMENTS

| | | | |
|---|---|---|---|
| 2,314,435 | 3/1943 | Allender | 585/332 |
| 2,389,984 | 11/1945 | Jones | 585/303 |
| 2,999,074 | 9/1961 | Bloch et al. | 252/442 |
| 3,073,878 | 1/1963 | Johnson | 585/712 |
| 3,112,351 | 11/1963 | Hoekstra | 585/748 |
| 3,172,834 | 3/1965 | Kozlowski | 208/58 |
| 3,249,650 | 5/1966 | Fenske | 585/706 |
| 3,391,218 | 7/1968 | Bloch | 585/660 |
| 3,409,540 | 11/1968 | Gould et al. | 208/79 |
| 3,448,165 | 6/1969 | Bloch | 585/660 |
| 3,506,733 | 4/1970 | Mayhue | 585/737 |
| 3,527,715 | 9/1970 | Giannetti et al. | 252/415 |
| 3,560,587 | 2/1971 | Borst, Jr. | 585/714 |
| 3,647,719 | 3/1972 | Hayes | 252/466 PT |
| 3,647,911 | 3/1972 | Vesely et al. | 585/660 |
| 3,649,704 | 3/1972 | Hayes | 585/482 |
| 3,650,943 | 3/1972 | Schuller | 208/60 |
| 3,742,078 | 6/1973 | Hayes | 585/434 |
| 3,745,112 | 7/1973 | Rausch | 208/139 |
| 3,755,481 | 8/1973 | Hayes | 585/434 |
| 3,789,082 | 1/1974 | Cook et al. | 585/748 |
| 3,925,502 | 12/1975 | Boney et al. | 585/720 |
| 3,931,352 | 1/1976 | Mikulicz | 585/332 |
| 4,139,573 | 2/1979 | Carson | 585/701 |
| 4,161,497 | 7/1979 | Makovec et al. | 585/714 |
| 4,275,255 | 1/1981 | Vora | 585/315 |

OTHER PUBLICATIONS

The Oil and Gas Journal, R. F. Anderson, "Changes Keep HF Alkylation Up-to-Date", Feb. 11, 1974, pp. 78–82.

Primary Examiner—Curtis R. Davis
Attorney, Agent, or Firm—James R. Hoatson, Jr.; John F. Spears, Jr.; William H. Page, II

[57] ABSTRACT

A hydrocarbon conversion process for producing $C_8$ hydrocarbons suitable for use as motor fuel blending components from normal butane or a mixture of isobutane and normal butane. A butane feed stream is fractionated to produce a normal butane stream which is passed through a butane isomerization zone. The effluent of the isomerization zone is admixed with isobutane and passed into a butane dehydrogenation zone. The $C_4$ effluent of the dehydrogenation zone is passed into an HF alkylation zone in which $C_8$ hydrocarbons are produced. The alkylation zone effluent stream is passed into the feed stream fractionator. Preferably, an isobutane stream is withdrawn from the feed stream fractionator and divided into a portion which is passed into the dehydrogenation zone and a portion passed into the alkylation zone based on a measurement of the isobutane inventory of the process.

14 Claims, 1 Drawing Figure

HYDROCARBON CONVERSION PROCESS FOR THE PRODUCTION OF GASOLINE

FIELD OF THE INVENTION

The invention is an integrated hydrocarbon conversion process for producing $C_8$ branched chain hydrocarbons suitable for use as gasoline blending stocks from normal butane or a mixture of isobutane and normal butane. The invention relates to such processes as the isomerization of light normal paraffins and the dehydrogenation of isoparaffins and normal paraffins. The invention also relates to processes for the fractionation of hydrocarbons and the alkylation of paraffins such as HF alkylation processes. The invention therefore relates to processes similar in nature to those described in U.S. patents classified in Classes 208, 210 and 585.

PRIOR ART

The production of motor fuel by the alkylation of light paraffins with $C_3$ and/or $C_4$ olefins is a widely practiced commercial process. Liquid phase hydrofluoric acid (HF) is often employed as the catalyst. This process is described in U.S. Pat. Nos. 3,073,878; 3,249,650; 3,560,587; 3,925,502 (Cl. 260-683.48); 4,139,573 (Cl. 260683.49); and 4,161,497 (Cl. 585-714). The process is also described in the article starting at page 78 of the Feb. 11, 1974 issue of *The Oil and Gas Journal*. These references describe process conditions, process equipment, the regeneration of the HF, and fractionation and treating procedures required in the process.

The isomerization of normal paraffins is described in U.S. Pat. Nos. 2,999,074; 3,112,351; 3,527,715 (Cl. 252-415); 3,649,704 (Cl. 260-668A); 3,789,082 and 3,506,733 (Cl. 260-683.68). These references are pertinent for their showing of the high level of development of the art of paraffin isomerization.

Processes for the dehydrogenation of paraffins are described in U.S. Pat. Nos. 3,391,218; 3,448,165; 3,647,911 (Cl. 260-683.3); 3,647,719 (Cl. 252-466PT); 3,742,078; and 3,755,481 (Cl. 260-668D). These references describe the catalyst and process conditions which may be employed in the dehydrogenation of butanes. The preferred dehydrogenation catalyst is described in U.S. Pat. No. 3,745,112 (Cl. 208-139).

A multi-step process in which normal butanes are isomerized and the resultant isobutane is consumed in an alkylation zone by reaction with olefinic hydrocarbons is described in U.S. Pat. No. 3,931,352 (Cl. 260-683.49). U.S. Pat. Nos. 3,409,540 and 3,650,943 also illustrate the sequential steps of butane isomerization and alkylation.

A motor fuel producing process which is pertinent because it utilizes the same four processing zones as the subject invention is described in U.S. Pat. No. 2,314,435. However, the flow path of the $C_4$ hydrocarbons between different zones, such as the fractionation and dehydrogenation zones, is significantly different than that of the subject invention.

An integrated process which links together a hydrocracking zone with a fractionation zone, a dehydrogenation zone and an alkylation zone is shown in U.S. Pat. No. 3,172,834. This reference is also pertinent because of its teaching of the division of an isobutane stream between the dehydrogenation zone and the alkylation zone. The overall flow of this reference is markedly different from the claimed process and lacks such features as an isomerization zone or butane recycle streams.

BRIEF SUMMARY OF THE INVENTION

The invention provides a hydrocarbon conversion process for the production of $C_8$ isoparaffins from a mixture of isobutane and normal butane. The process features a novel integrated flow path and also a control method which splits an isobutane-rich stream in a manner which compensates for changes in the feed stream composition or in the operation of the butane isomerization zone or other zones.

One embodiment of the invention may be characterized as a hydrocarbon conversion process which comprises the steps of passing a feed stream which comprises a mixture of isobutane and normal butane into a fractionation zone; removing a first process stream, which is rich in normal butane, from the fractionation zone and passing the first process stream into a butane isomerization zone operated at isomerization conditions to produce a butane isomerization zone effluent stream which comprises isobutane and normal butane; passing the butane isomerization zone effluent stream and a hereinafter characterized second process stream into a butane dehydrogenation zone operated at dehydrogenation conditions to produce a dehydrogenation zone effluent stream which comprises isobutane, normal butane, isobutylene, butene-1 and butene-2; passing the butane dehydrogenation zone effluent stream into an alkylation zone operated at alkylation conditions to produce an alkylation zone effluent stream which comprises isobutane, normal butane and $C_8$ branched chain hydrocarbons; passing the alkylation zone effluent stream into the fractionation zone; removing a third process stream, which is rich in isobutane, from the fractionation zone, passing a first portion of the third process stream into the alkylation zone and passing a second portion of the third process stream into the butane dehydrogenation zone as at least a portion of said second process stream; and removing a net product stream comprising $C_8$ branched chain hydrocarbons from the fractionation zone.

In a more limited embodiment of the invention, the division of the third process stream, which is rich in isobutane, is regulated by measuring a value representative of the total isobutane inventory of the process. Preferably, the upper liquid level in a surge drum through which the third process stream flows is the measured value used to control the division of the third process stream.

BRIEF DESCRIPTION OF THE DRAWING

A butane feed stream from line 1 is separated in an isostripper 2 into a normal butane-rich stream passed into an isomerization zone 7 through line 6 and an isobutane-rich stream carried by lines 4 and 25. The resulting isomerate and a portion of the isobutane stream enter the butane dehydrogenation reaction zone 14 through line 13, with the $C_4$-plus portion of the effluent of this zone passing through lines 18 and 19 to an alkylation reactor 20. Changes in the isobutane inventory of the plant are reflected in the change in the level in the surge drum 24. This level is monitored to regulate the operation of a valve 27 which divides the isobutane-rich stream between the alkylation zone and the dehydrogenation zone.

DETAILED DESCRIPTION

There has been a constantly increasing demand for high octane gasoline blending stocks. This is in part the result of the gradual phase down in the use of lead anti-knock compounds in gasoline. It also results from the steadily increasing number of motor vehicles which must be fueled with lead-free gasoline to prevent damage to the catalytic converters used in pollution reduction systems. For these and other reasons, it has become increasingly important to maximize both the quantity and the octane number of gasoline which is produced from available hydrocarbon feedstocks.

New facilities for the recovery of light hydrocarbons, such as propane and butane, which were previously wasted by flaring close to the site of their production are now coming on-stream in several Mideastern countries. There is presently no shortage of propane or butane on a worldwide basis, and the added production of propane and butane may result in there being an actual surplus of these light hydrocarbons.

It is an objective of the subject invention to provide a hydrocarbon conversion process for producing high octane motor fuel blending stocks. It is also an objective of the subject invention to provide an improved process for converting butane into gasoline.

A further objective is to provide a flexible process for converting butane to gasoline which can compensate for variations in feed composition or conversions achieved within the process. Another objective of the subject invention is to provide a process for converting butane into a normally liquid hydrocarbon which is easily conveyed in conventional liquid carrying transports.

The feed stream to the subject process will normally contain a mixture of isobutane and normal butane. Since this feed stream is expected to be derived from natural gas, the concentration of normal butane is expected to be several times greater than the concentration of isobutane. It is preferred that over 95 mol.% of the feed stream is $C_4$ hydrocarbons. It is also preferred that the feed stream contains as little $C_3$-minus hydrocarbons as is practical. Several mol.% of $C_5$-plus hydrocarbons is acceptable. The feed stream is passed into a first fractionation zone, which preferably comprises a single trayed column. As used herein, the term "fractionation zone" is intended to refer to the process equipment in which a specified separation is performed by fractional distillation and may include one or more fractionation columns as desired. A fractionation zone will also comprise such auxiliary equipment as reboilers, overhead vapor condensers and overhead receivers as may be required.

The single column which functions as the first fractionation zone is referred to herein as the isostripper or isostripper column following the customary practice in the art of motor fuel alkylation processes. It is the function of the deisobutanizer column to separate the several entering streams into a net overhead stream, an upper sidecut stream which is rich in isobutane, a lower sidecut stream which is rich in normal butane and a bottoms stream comprising some normal butane but being rich in heavier hydrocarbons such as pentanes and octanes. As used herein, the term "rich" is intended to indicate that a process stream contains at least 55 mol.% of the particular hydrocarbon which is specified. It is believed that in most cases, a column containing about 60 actual trays will function adequately as the deisobutanizer when correctly designed and operated. A representative set of operating conditions includes an overhead vapor temperature of approximately 60° C. and a pressure of about 140 psig.

Figure 1:
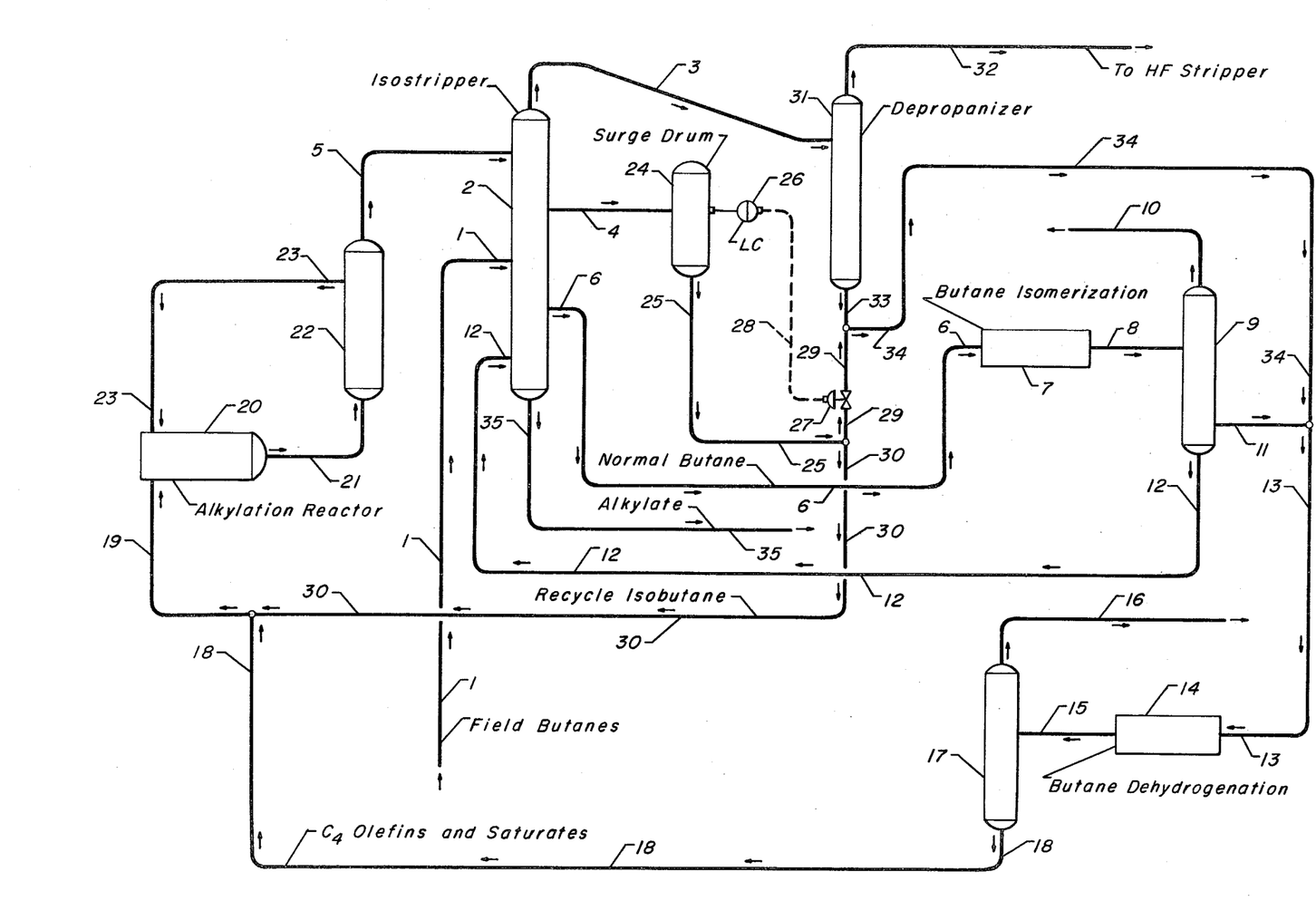

The subject process revolves around the isostripper. The feed stream enters this column and the product stream is removed from the column. At least three other process streams are also withdrawn from the isostripper. These include an isobutane-rich sidecut stream and a normal butane-rich sidecut stream. In the subject process, all of the normal butane-rich sidecut stream is passed into an isomerization zone following alumina treating to remove combined fluorides, while the isobutane-rich sidecut stream is normally divided between an alkylation zone and a dehydrogenation zone. Essentially all of the $C_4$ hydrocarbons leaving the isomerization zone are also passed into the dehydrogenation zone. The effluent of the dehydrogenation zone is fed into the alkylation zone. The effluent of the alkylation zone is passed into the isostripper thereby completing the loop through the process. This flow of the various hydrocarbon streams through the process may be more easily understood by an examination of the Drawing.

Referring now to the Drawing, a feed stream of field butanes comprising a mixture of normal butane and isobutane enters the process through line 1 and is passed into the isostripper 2 at an intermediate point. The customary fractional distillation operation which occurs within the isostripper separates the entering hydrocarbons into four effluent streams. One of these streams is a lower sidecut stream removed through line 6 which is rich in normal butane. This normal butane stream is passed into the butane isomerization zone which comprises the butane isomerization reactor system 7 and a stripping column 9 as the feed stream to this zone. The effluent stream of the isomerization reactor system is passed into the light ends stripping column through line 8. Light ends such as hydrogen, methane and propane are removed from this column as a net overhead stream carried by line 10. The remaining hydrocarbons which enter the stripping column 9 are separated into a $C_5$-plus fraction which is removed as a bottoms stream through line 12 and a butane isomerate stream removed as a lower sidecut through line 11 and referred to herein as the isomerization zone effluent stream.

This butane isomerate stream contains a mixture of isobutane and normal butane and is admixed with an isobutane-rich stream carried by line 34. It is then passed through line 13 into a butane dehydrogenation zone which comprises a butane dehydrogenation reactor system 14 and a second stripping column 17. The effluent of the butane dehydrogenation reactor system is passed into the light ends stripping column through line 15. Light hydrocarbons, such as methane and propane, and any hydrogen which enters the light ends stripping column are removed from this column as a net overhead stream through line 16. This produces a stripping column bottoms stream carried by line 18 which comprises substantially all of the normal butane, isobutane, and butylenes entering the column and which is referred to herein as the butane dehydrogenation zone effluent stream.

The admixture of $C_4$ olefins and saturates flowing through line 18 is combined with any recycle isobutane passing through line 30 and is then pased into an alkylation reactor 20 through line 19. A recycle stream of liquid phase HF is passed into the alkylation zone through line 23. An emulsion made up of the acid-catalyst, unconverted hydrocarbons and product hydrocarbons, commonly referred to as alkylate, is removed from the alkylation reactor in line 21 and passed into the lower end of a combination soaking zone and acid-hydrocarbon separator 22. As the emulsion rises through the lower portion of the vessel 22, it is subjected to agitation caused by the liquid flowing through various restrictions in order to maintain the emulsion. When this emulsion reaches an upper portion of the vessel, it enters a quiescent separation zone which allows the denser HF to separate from the less dense hydrocarbons. The HF is trapped out and recycled to the alkylation reactor through line 23. The remaining hydrocarbons are a mixture of the product hydrocarbons, commonly referred to as alkylate, unconsumed isobutane, normal butane and small amounts of propane and pentane. These hydrocarbons are passed into the isostripper through line 5 as the alkylation zone effluent stream.

Some HF is dissolved in the hydrocarbons flowing through line 5. This HF together with a small amount of propane formed in the alkylation reactor, any propane in the feed stream, and some isobutane constitutes the majority of a net overhead vapor stream removed from the isostripper in line 3. This stream is passed through an overhead condenser not shown and then into an overhead separator which is also not shown. A great majority of the HF originally present in the isostripper overhead vapor stream is condensed and forms a separate liquid phase in the overhead receiver which allows its recycling by a line not shown to the alkylation reactor. The hydrocarbon portion of the isostripper overhead stream is withdrawn from this overhead receiver and passed into the depropanizer 31. This hydrocarbon stream basically comprises a mixture of propane and isobutane but also contains a small amount of dissolved HF. Essentially all of the HF and propane which enter the depropanizer are concentrated into the depropanizer overhead vapor stream which is passed through line 32 to the overhead condensing system shared in common with the HF stripper present in most alkylation units. This overhead vapor stream is combined with the overhead vapor stream of the HF stripper column, not shown in the drawing, passed through an overhead condenser and into a second overhead receiver from which the condensed HF is withdrawn by decantation. Liquid phase propane is removed from this overhead receiver, with a portion being passed into the depropanizer as reflux and a second portion being passed into the HF stripper. In the HF stripper, essentially all HF dissolved in the entering liquid phase propane is concentrated into an HF stripper overhead stream such that a stream of high purity by-product propane may be withdrawn from the process for suitable treatment. The design or operation of this overhead system does not form a part of the inventive concept and therefore has not been illustrated. All of the isobutane which enters the depropanizer 31 is concentrated into a net depropanizer bottoms stream carried by line 33, which preferably is passed directly into line 34 for passage into the butane dehydrogenation zone.

An upper sidecut stream which is rich in isobutane is removed from the isostripper in line 4 and passed into a surge drum 24. This stream will contain small amounts of alkylate and normal butane. A typical upper sidecut stream may contain 85 mol.% isobutane and 10 mol.% normal butane, with the remainder being propane and alkylate. The isobutane-rich liquid is removed from the surge drum through line 25 and is then passed into either or both lines 29 and 30. A level control means 26 monitors the level of the isobutane-rich liquid in the surge drum and transmits a signal through means 28 to a flow control valve 27 located in line 29. When the level of the isobutane-rich liquid increases above a set limit, the level control means activates the controller of the flow control valve 27 such that the flow control valve either opens or opens to a greater extent so that the flow of the isobutane-rich liquid through line 29 is increased. In this manner, the process automatically responds to a buildup in the isobutane inventory of the process by passing an additional amount of isobutane through lines 34 and 13 into the butane dehydrogenation zone wherein the isobutane is partially converted to isobutylene. Likewise, if the inventory of isobutane in the process begins to fall below a desired level as monitored by the level within the surge drum, then the flow of isobutane to the dehydrogenation zone is decreased by closing valve 27 and recycling the isobutane through line 30. This reduces the rate at which isobutane is consumed in the process.

The $C_5$-plus hydrocarbons which were concentrated into the net bottoms stream of the light ends stripper 9 are passed into the isostripper through line 12. These hydrocarbons and the alkylate produced in the alkylation reactor 20, which is predominately branched $C_8$ paraffins, is removed from the isostripper in line 35 as the net product of the process. This product has a high octane number and is highly suitable for use as a gasoline blending stock.

This description of the preferred embodiment of the invention is not intended to preclude from the scope of the inventive concept those other embodiments which are set out herein or which are the result of normal and expected modification of those embodiments. For clarify of presentation of the inventive concept, various pieces of apparatus and systems necessary for the practice of the invention, such as heat exchangers, control systems, fractionator internals, reboiling and overhead condensing systems, etc., have not been illustrated.

The broadest embodiments of the subject invention do not require the division of the isobutane-rich stream withdrawn from the isostripper. However, this division is preferred. The exact mechanism employed to divide the flow of the isobutane-rich stream between the alkylation zone and the dehydrogenation zone is subject to considerable variation. The flow control system may comprise either one or two valves, with the placement of the valve or valves being dependent on such factors as the pressures employed in the alkylation and dehydrogenation zones, the placement of pumps used to circulate various streams and the pressure drop caused by fluid flow through the different transfer lines. The level control system on the surge drum, which preferably is a vertical cylindrical vessel, may include any of several well known liquid level sensing means. This level sensor may employ movable floats, capacitance probes, etc. An electronic or pneumatic controller of customary design would receive a signal from the liquid level sensor and generate an appropriate signal for transmission to the valve means.

The liquid level within the surge drum is a representative measure of the isobutane inventory of the entire process when the process is lined out at steady state conditions. An increase in this level indicates isobutane is being charged to the process at a greater rate than it is being consumed. A decrease in this level indicates isobutane is being consumed at too high a rate. Some of the isobutane which is charged to the dehydrogenation zone will be dehydrogenated to isobutylene. This isobutylene subsequently enters the alkylation zone where it alkylates with isobutane, further reducing the isobutane inventory. Substantially, all isobutylene produced in this way is converted to alkylate in the alkylation zone. Increasing the amount of isobutane which enters the dehydrogenation zone thereby increases the rate of isobutane consumption in the overall process and should reduce the isobutane inventory of the processing equipment. The flow of the isobutane-rich stream withdrawn from the isostripper is therefore split between the dehydrogenation zone and alkylation zone as required to bring the isobutane inventory into balance. This provides a means of automatically compensating for many variables such as the isobutane content of the feed stream, the operation of the isomerization and dehydrogenation zones, etc.

If the rate of isobutane consumption within the process exceeds the rate at which isobutane is made available, it may be necessary to pass a supplemental isobutane feed stream into the process through a line not shown. The total rate at which isobutane is made available for consumption within the process is the sum of the rate of isobutane production in the isomerization zone plus the isobutane feed rate in the mixed butane feed stream. An isobutane deficiency will most likely be caused by a low isobutane concentration in the mixed butane feed stream. If isobutane is being consumed within the process at a greater rate than it can be made available for consumption, this may be adjusted for by the passage of all of the isobutane sidecut stream into the alkylation zone. In addition, the isobutane-rich bottoms stream of the depropanizer could be passed into the alkylation zone instead of the dehydrogenation zone. The entire contents of line 33 could in this variation be made to flow through line 29 into line 30.

The net hydrocarbonaceous effluent of the alkylation zone is passed into the fractionation zone which preferably comprises only the single isostripper column. In many respects this column functions in a manner similar to the isostripper column present in many HF alkylation units which produce motor fuel alkylate. The hydrocarbonaceous alkylation zone effluent stream preferably enters the isostripper at an upper intermediate point separated from the top of the isostripper by several fractionation trays. The isobutane-rich sidecut stream is removed from the isostripper several trays below this point. A normal butane-rich sidecut is removed from the isostripper at a lower intermediate point, and the field butane feed stream is passed into the isostripper at a point between the two sidecut drawoffs. The lower normal butane-rich sidecut stream will also contain heavy hydrocarbons such as pentane and $C_8$ alkylate.

Propane and other light hydrocarbons which are present in the feed stream to the alkylation zone will enter the isostripper as part of the alkylation zone effluent stream. The propane is concentrated into the net overhead vapor of the isostripper. The overhead of the isostripper will also contain isobutane and HF if HF is used as the alkylation catalyst. As previously described, this overhead stream is preferably passed through a condenser and the resultant condensate is then separated into a liquid hydrocarbon stream and a liquid HF stream in an overhead receiver which functions as a phase separation vessel. The liquid phase HF is recycled to the alkylation zone and the hydrocarbon phase is passed into a second fractionation column referred to as a depropanizer, preferably near the top of this column. All of the HF dissolved in the hydrocarbon phase is concentrated into the overhead stream of the depropanizer, with this overhead stream being passed into a condenser and a second overhead receiver which acts as a separator. The HF is then separated by decantation and returned to the alkylation unit. The liquid hydrocarbon from the second overhead receiver is passed into a third fractionation column referred to as an HF stripper. The bottoms stream of the depropanizer is relatively high purity isobutane and is passed directly into the butane dehydrogenation zone.

The overhead vapor stream of the HF stripper column comprises some propane and essentially all of the HF dissolved in the entering hydrocarbons. Preferably, this overhead stream is passed into the same condenser and overhead receiver as the depropanizer overhead stream. The bottoms stream of the HF stripper is high purity propane which is passed through an alumina treater for the removal of residual HF and is then withdrawn from the process.

The alkylate present in the net alkylation zone effluent stream is concentrated into a net isostripper bottoms stream. If desired, this bottoms stream may be admixed directly with the rather small bottoms stream of the isomerization zone stripping column, which contains normal butane and any $C_5$-plus hydrocarbons which enter the isomerization zone. This allows the rejection of any $C_5$-plus hydrocarbons which enter the isomerization zone from the process and also facilitates the addition of normal butane to the final product. Some normal butane is normally required to be present in the alkylate to increase its vapor pressure up to that specified for gasoline. If the net alkylate product is intended for lengthy storage or transportation, it may be advisable to minimize the butane content of the product and to thereby lessen vaporization losses. The butane can then be blended into the alkylate at a later time. It is preferred that the bottoms stream of the isomerization zone stripping column is passed directly into the isostripper column as shown in the Drawing.

The normal butane-rich sidecut stream removed from the isostripper is passed into a butane isomerization zone. This zone comprises a reactor system including a reactor and auxiliary process equipment such as heaters, condensers, separatory vessels, etc. The isomerization zone also contains a stripping column which eliminates hydrogen and light ends (methane and ethane) from the net effluent of the isomerization zone. With the preferred catalyst, this stripping column will also remove volatile chloride compounds from the isomerization zone effluent. The core of the operation of this zone is passage of the sidecut stream through a reactor maintained at butane isomerization-promoting conditions including the presence of an acidic isomerization catalyst. This is normally a relatively low pressure operation performed at a pressure of from about 50 to 600 psig. and at an elevated temperature as required by the activity of the catalyst. The average reactant temperature may be as high as 500° C., but is preferably between 100° C. and 320° C. It is normal practice to pass the butane through the reactor in admixture with between 1 and 10 moles of hydrogen per mole of butanes to ensure vapor phase conditions and to suppress coke deposition on the catalyst. It is preferred that the butane is passed vertically through one or more fixed beds of catalyst located within the reactor at a liquid hourly space velocity between 1.0 and 6.0, but space velocities in the broad range of 0.5 to 12.0 can be employed if desired.

The effluent of the isomerization reactor is normally separated into the hydrogen-rich recycle gas which is returned to the reactor and an isomerate-containing liquid stream. It is within the scope of the inventive concept that this liquid stream may be fractionated to allow the recycling of normal butanes and the achievement of high conversion rates, but this is not preferred. The isomerate-containing liquid removed from the reaction zone separator is preferably passed into a stripping column where $C_3$-minus light ends are removed to produce a net isomerization zone effluent stream containing over 90 mol.% $C_4$ hydrocarbons and which is removed from the stripping column as a sidecut stream. The term "butane isomerization zone effluent stream" is intended to refer to such a sidecut stream if a stripping column is utilized in the isomerization zone. Preferably, the $C_8$ alkylate and $C_5$ hydrocarbons which enter the isomerization zone in the feed are concentrated into a rather small stripping column bottoms stream which is recycled to the isostripper. Further details on the butane isomerization step of the subject process may be obtained by referring to the previously cited references.

The preferred isomerization-promoting catalyst for use in the isomerization zone comprises a platinum group component and a halogen component supported by an inorganic oxide carrier. In general, the carrier material is a porous, high surface area material which is relatively refractory to the conditions utilized in the isomerization process. The carrier material may be selected from silica, alumina, titanium dioxide, chromium, or mixtures of the oxides; various naturally occurring refractory oxides in different degrees of purity, such as bauxite and bentonite clay; or a diatomaceous earth such as kieselguhr. Of the above-mentioned oxides, alumina is preferred and particularly preferred is a synthetically prepared subtantially anhydrous gamma-alumina with a high degree of purity.

The preferred platinum group component is platinum, palladium or a mixture of platinum and palladium. This however is not intended to exclude the other platinum group metals such as rhodium, ruthenium, osmium and iridium. A platinum group component may exist within the final catalytic composite as an oxide, a sulfide or a halide, etc., or as an elemental metal. On a weight basis, the platinum group component will comprise only a minor fraction of the total catalytic material. The preferred catalyst will therefore contain less than about 2.0 wt.% of the platinum group component, with the preferred concentration being from about 0.05 to about 1.0 wt.%. The method by which the platinum group component is made part of the catalytic composite is not controlling. It may therefore be added by coprecipitation or cogelation with the preferred carrier material or by ion-exchange or impregnation on the pre-existing carrier material. The preferred method of preparing the catalyst impregnated the carrier material by contacting it with an aqueous solutin of a water-soluble, decomposable compound of a platinum group metal. This may be performed by dipping the carrier material in a solution of chloroplatinic acid, ammonium chloroplatinate, bromoplatinic acid, or platinum dichloride. The utilization of a platinum chloride compound is preferred since it facilitates the incorporation of both the platinum component and at least a minor quantity of the halogen component in a single step.

There are also numerous ways in which to add the halogen component to the isomerization catalyst. The halogen component may be composited with the carrier material during the impregnation of the carrier material with the platinum group component by the utilization of a mixture of chloroplatinic acid and hydrogen chloride. Alternatively, the alumina hydrosol which is typically utilized to form the preferred alumina carrier material may contain at least a portion of the halogen. The halogen may also be added by contacting a calcined carrier material with an aqueous solution of an acid such as hydrogen chloride, hydrogen fluoride, or hydrogen bromide, etc. The halogen component may be selected from chlorine, fluorine, iodine, bromine or mixtures thereof with chlorine and fluorine being particularly preferred. The halogen component is normally referred to as a combined halogen and is typically present in an amount of from 0.01 to about 5.0 wt.% based on the dried support material.

A particularly preferred method for the production of an isomerization catalyst is presented in U.S. Pat. No. 2,999,074. The carrier material and the platinum group component are composited and the resulting material is mildly calcined. This calcination is normally carried out under carefully controlled conditions to remove physically adsorbed solvents such as water but to retain some chemically combined hydroxyl groups on the surface of the catalyst. Temperatures ranging from 350° C. to about 700° C. are usually satisfactory. The calcined composite is then reacted with a metal halide of the Friedel-Crafts type. Suitable metal halides include aluminum chloride, aluminum bromide, ferric chloride and zinc chloride, etc. Of these, aluminum chloride is particularly preferred.

Recently developed isomerization catalysts are of a bimetallic or trimetallic nature. An example of this is the catalytic composite comprising a platinum group component, a germanium component, and a Friedel-Crafts metal halide component shown in U.S. Pat. No. 3,649,704. In U.S. Pat. No. 3,642,697, there is disclosed a trimetallic catalyst comprising a platinum group component, a germanium component, a rhenium component and a Friedel-Crafts metal halide component.

The net hydrocarbon effluent of the isomerization zone is a mixture of isobutane and normal butane. This stream and the isobutane-rich recycle stream produced by the admixture of the depropanizer bottoms with any of the upper isostripper sidecut stream which is to be passed into the dehydrogenation zone are then passed into the butane dehydrogenation zone wherein in a portion of these butanes are converted into the corresponding butylenes. This zone will contain a reaction zone and associated auxiliary process equipment as is required for the operation of the reaction zone. The auxiliary equipment should include coolers, condensers and a vapor-liquid separator designed and operated to produce hydrogen-rich recycle and net gas streams and a liquid-phase hydrocarbon stream. The separator may be operated at a temperature of $-40°$ C. and a pressure of 200 psig. The separation facilities of the dehydrogenation zone preferably includes at least one fractionation column, which receives the liquid-phase hydrocarbons withdrawn from the separator. This column is designed and operated to eliminate most propane and substantially all ethane and lighter boiling components from the net dehydrogenation zone effluent stream. The removal of ethane is necessary since the carry-over of this light material into an HF alkylation zone will interfere with the desired recovery of HF in the isostripper-depropanizer system of the alkylation zone. If a different alkylation catalyst is used, the presence of ethane in the alkylation zone feed stream may be acceptable. Propylene may be present at this point in the process due to the dehydrogenation of propane found in the feed stream to the process or from the cracking of butanes and the production of the light ends removed from this zone.

The reaction zone of the butane dehydrogenation zone preferably comprises at least one radial flow reactor in which the catalyst gradually moves downward by gravity flow to allow the continuous replacement of used catalyst with catalyst having a higher activity. It is preferred that a multi-stage moving bed reactor is employed. A detailed description of moving bed reactors of this type may be obtained by reference to U.S. Pat. Nos. 3,647,680; 3,652,231; 3,706,536; 3,785,963; 3,825,116; 3,839,196; 3,839,197; 3,854,887; and 3,856,662.

The particular dehydrogenation conditions employed within the dehydrogenation zone may vary depending on such factors as the catalyst activity and the desired conversion. The conditions normally employed for butane dehydrogenation include a temperature of from about 500° C. to 700° C., a pressure of from 0.5 to about 10 atmospheres and a liquid hourly space velocity of about 1 to 20 hr.$^{-1}$. The preferred operating temperature will be within the range of from about 550° C. to 650° C., and the preferred operating pressure is about 0.5 to 3 atmospheres.

The preferred butane dehydrogenation catalyst is comprised of a platinum group component, a tin component and an alkali metal component with a porous inorganic carrier material. Other catalytic compositions may be used within this zone if desired.

It is preferred that the porous carrier material is an absorptive high surface area support having a surface area of about 25 to about 500 m$^2$/g. The porous carrier material should be relatively refractory to the conditions utilized in the reaction zone and may be chosen from those carrier materials which have traditionally been utilized in dual-function hydrocarbon conversion catalysts. A porous carrier material may therefore be chosen from an activated carbon, coke or charcoal, silica or silica gel, clays and silicates including those synthetically prepared and naturally occurring which may or may not be acid-treated, as for example attapulgus clay, diatomaceous earth, kieselguhr, bauxite; refractory inorganic oxides such as alumina, titanium dioxide, zirconium dioxides, magnesia, silica-alumina, alumina-boria, etc.; crystalline aluminosilicates such as naturally occurring or synthetically prepared mordenite or a combination of one or more of these materials. The preferred porous carrier material is a refractory inorganic oxide with the best redsults being obtained with an alumina carrier material. The crystalline aluminas, such as gamma-alumina, give the best results. In general, the preferred catalysts will have an alumina carrier which is in the form of spherical particles having a relatively small diameter on the order of about 1/16-inch.

The preferred alumina carrier material may be prepared in any suitable manner. For example, the alumina carrier may be prepared by adding a suitable alkaline reagent, such as ammonium hydroxide to a salt of aluminum such as aluminum chloride in an amount to form an aluminum hydroxide gel which upon drying and calcining, is converted to alumina. It is particularly preferred that alumina spheres are manufactured by the well-known oil drop method which comprises forming an alumina hydrosol by the techniques taught in the art, and preferably by reacting aluminum metal with hydrochloric acid, and combining the hydrosol with a suitable gelling agent. The resultant mixture is dropped into an oil bath maintained at elevated temperatures. The droplets remain in the oil bath until they set and form hydrogel spheres. The spheres are then continuously withdrawn from the oil bath and are normally subjected to specific aging treatments in oil and an ammoniacal solution to further improve their physical characteristics. The resulting pellets are then washed and dried at relatively low temperatures of about 150° C. to about 200° C. and calcined at a temperature of about 450° C. to about 700° C. for a period of about 1 to about 20 hours. See the teachings of U.S. Pat. No. 2,620,314 for additional details on the preparation of the base material by the oil drop method.

The preferred dehydrogenation catalyst also contains a platinum group component. Of the platinum group metals, which include palladium rhodium, ruthenium, osmium and iridium, the use of platinum is preferred. The platinum group component may exist within the final catalyst composite as a compound such as an oxide, sulfide, halide, oxysulfide, etc., or as an elemental metal or in combination with one or more other ingredients of the catalyst. It is believed that best results are obtained when substantially all the platinum group component exists in the elemental state. The platinum group component generally comprises from about 0.01 to about 2 wt. % of the final catalytic composite, calculated on an elemental basis. It is preferred that the platinum content of the catalyst is between about 0.1 and 1.0 wt. %. The preferred platinum group component is platinum, with palladium being the next preferred metal. The platinum group component may be incorporated into the catalytic composite in any suitable manner such as by coprecipitation or cogelation with the preferred carrier material, or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinic or chloropalladic acid. An acid such as hydrogen chloride is generally added to the impregnation solution to aid in the distribution of the platinum group component throughout the carrier material.

The tin component of the preferred catalyst should constitute about 0.01 to about 5 wt. % of the final composite, calculated on an elemental basis, although substantially higher amounts of tin may be utilized in some cases. Best results are often obtained with about 0.1 to about 1 wt. % tin. It is preferred that the atomic ratio of tin to platinum is between 1:1 and about 6:1. The tin component may be incorporated into the catalytic composite in any suitable manner known to effectively disperse this component in a very uniform manner throughout the carrier material. Thus the component may be added to the carrier by coprecipitation. However, a preferred method of incorporating the tin component involves coprecipitating it during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into the oil bath as previously described. The tin component may also be added through the utilization of a soluble, decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

The preferred butane dehydrogenation catalyst contains less than 0.5 wt. % halogen and preferably less than 0.1 wt. % halogen. Residual amounts of any halogen, such as chlorine, at or below this concentration may be tolerated. The preferred catalyst does however contain an alkali metal component chosen from cesium, rubidium, potassium, sodium, and lithium. The preferred alkali metals are potassium and lithium. The concentration of the alkali metal may range from between 0.05 and 3.5 wt. %, but is preferably between 0.2 and about 1.5 wt. % calculated on an elemental basis.

The net $C_4$-plus effluent of the dehydrogenation zone is passed into an alkylation zone. A portion of the isobutane-rich sidecut stream removed from the isostripper will also be passed into the alkylation zone. These two streams may be admixed prior to their passage into the alkylation zone or may enter as separate streams. The dehydrogenation zone effluent stream may contain some propylene formed by the dehydrogenation of propane present in the feed stream. This propylene is consumed in the same manner as the butylenes by reaction with the isobutane. The term "alkylation zone" is intended to indicate a sequence of processing equipment in which the entering reactants are contacted with an alkylation catalyst maintained at alkylation-promoting conditions including one or more reaction zones and the required equipment for the separation and recovery of the resultant alkylate from process streams within the alkylation zone. It is preferred that the alkylation zone contains no fractionation columns other than that used for catalyst regeneration.

The alkylation reaction is normally promoted by the presence of a mineral acid catalysts such as hydrofluoric acid, sulfuric acid or phosphoric acid. Hydrofluoric acid is the preferred catalyst. These acids are maintained in a liquid phase containing a minimum of water to reduce corrosion problems. The maximum amount of water normally allowed in the acid is about 5 wt. %. When fresh acid is charged to a plant, it is normally very dry and contains about 0.5 wt. % water or less. The catalyst may also comprise a mixture of a mineral acid and a Friedel-Crafts meal halide promoter such as aluminum chloride, aluminum bromide, boron trifluoride and other proton donors.

Alkylation conditions in general include a pressure sufficient to maintain the hydrocarbons and acid in a liquid phase, with a general range being from about 20 psig. to about 500 psig., and a more preferred range being from 100 psig. to about 250 psig. It is preferred that the pressure within the reactant-catalyst contacting vessel is approximately 150 psig. and essentially "floats" on pressure maintained in the downstream isostripper. Although the alkylation reaction may be performed at temperatures from below $-18°$ C. to about 90° C., it is preferred to operate the commercially prevalent isoparaffin-olefin alkylation process in the range of from about 10° C. to about 60° C., with 32° C. being a representative and particularly preferred operating temperature.

Typical operating conditions in the alkylation zone include a high ratio of the concentration of the isoparaffinic or other alkylatable material to the concentration of the olefinic material in order to produce a high quality alkylate by encouraging monoalkylation instead of polymerization. A broad range of this ratio is from about 6 to about 20 with a preferred operating range being from 8 to 12. A second ratio which varies in competing alkylation processes is the ratio of the acid to the hydrocarbons in the total emulsion formed, that is, the ratio in the material charged to the mixing zone or reaction point. This ratio may vary widely from a high of about 10:1 to a low of about 0.5:1, but it is preferred that the subject process is operated at an acid to hydrocarbon ratio of about 2:1.

There are a great number of olefin-isoparaffin alkylation processes known to those skilled in the art. The great majority of these processes will operate within the range of alkylation conditions set out above. They would however have substantial differences in equipment and flow paths used in performing the alkylation. These variations are attempts to obtain optimum quality alkylate by varying the method of contacting the mono-olefin with the isoparaffin. Since this reaction occurs very rapidly, and also because hydrofluoric acid will catalyze the polymerization of the mono-olefin, the standard alkylation methods consist of either first admixing acid-free streams of olefin and isoparaffin to form a reactant mixture which is then admixed with the hydrofluoric acid, or an acid-free olefin stream is mixed with an acid-containing isoparaffin stream. In either case, a large number of ventures or mixing nozzles are normally utilized to quickly disperse the olefin-containing stream into the acid-containing stream.

The resulting alkylation reaction is very exothermic and it is therefore necessary to provide means to remove the heat of reaction. This is normally done either by providing indirect heat-exchange means within the reacting mixture or by cooling one of the reactant streams, normally the acid stream, prior to passing it to the reaction zone. Mixing the acid and hydrocarbon feed stream results in the formation of an emulsion, and it is preferred that this emulsion be maintained by the continued agitation of the emulsion since this results in the removal of fluorides from the alkylate and the improvement of the octane number of the resulting alkylate. The maintenance of the emulsion is normally effected by its passage through a mixer or soak zone comprising a vessel having a number of internal obstructions which produce substantial turbulence as the emulsion passes through them. The emulsion is then typically fed into some type of settling vessel wherein a gravity separation of the emulsion is performed. The acid phase is removed for recirculation, and the recirculated acid may be cooled to remove the heat of reaction. The hydrocarbon phase removed from the mixer-settler is passed into the isostripper. This hydrocarbon phase will comprise mainly alkylate and the excess isobutane which was fed to the alkylation zone. Some processes do not utilize a soak zone at all and still others contact the separated hydrocarbon phase with a regenerated high strength acid stream to aid in defluorination. Further details on the design and operation of reaction vessels, the overall operation of the alkylation step, the regeneration of the preferred HF catalyst, etc., may be obtained by referring to the previously cited references.

The net hydrocarbonaceous effluent stream of the alkylation zone is passed into the isostripper. As previously mentioned, this isostripper is similar to that normally associated with many HF catalyst motor fuel alkylation units. The isostripper recovers the $C_8$ alkylate and other $C_5$-plus hydrocarbons as a net bottoms stream removed as the product of the process. When HF is used as the alkylation catalyst, the bottoms stream contains a small amount of isopentane produced in the alkylation zone. Some propane is also produced in the alkylation zone in this instance. If HF is utilized as the catalyst in the alkylation zone, fluoride compounds will normally be present in the bottoms stream and the side-cut streams. These streams should be passed through a fluoride removal zone comprising an alumina treater and a caustic contacting zone when the fluoride compounds will be detrimental to any catalyst which they may subsequently contact. This is often the case with chloride-promoted isomerization catalyst. Such treatment is required with the preferred isomerization catalyst.

In accordance with this description, one embodiment of the inventive concept may be broadly characterized as a hydrocarbon conversion process which comprises the steps of passing a feed stream which comprises normal butane into a fractionation zone; removing a first process stream, which is rich in normal butane, from the fractionation zone and passing the first process stream into a butane isomerization zone operated at isomerization conditions to produce a butane isomerization zone effluent stream which comprises isobutane and normal butanes; passing the butane isomerization zone effluent stream and a hereinafter characterized second process stream into a butane dehydrogenation zone operated at dehydrogenation conditions to produce a dehydrogenation zone effluent stream comprising isobutane, normal butane, and butylenes; passing the butane dehydrogenation zone effluent stream into an alkylation zone operated at alkylation conditions to produce an alkylation zone effluent stream which comprises isobutane, normal butane and $C_8$ hydrocarbons; passing the alkylation zone effluent stream into the fractionation zone; removing a third process stream, which is rich in isobutane, from the fractionation zone and passing at least a portion of the third process stream into the alkylation zone; removing a fourth process stream, which comprises propane and isobutane, from the fractionation zone and passing substantially all of the hydrocarbons present in the fourth process stream into a depropanizer column; removing an isobutane-rich fifth process stream from the depropanizer column and passing the fifth process stream into the butane dehydrogenation zone as at least a portion of said second process stream; and removing a net product stream comprising saturated $C_8$ hydrocarbons from the fractionation zone.

I claim as my invention:

1. A hydrocarbon conversion process which comprises the steps of:
   (a) passing a feed stream which comprises normal butane into a fractionation zone comprising one fractionation column;
   (b) removing a first process stream, which is rich in normal butane, from the fractionation zone and passing the first process stream into a butane isomerization zone operated at isomerization conditions to produce a butane isomerization zone effluent stream which comprises isobutane and normal butane;
   (c) passing the butane isomerization zone effluent stream and a hereinafter characterized second process stream into a butane dehydrogenation zone operated at dehydrogenation conditions to produce a dehydrogenation zone effluent stream comprising isobutane, normal butane, and butylenes;
   (d) passing the butane dehydrogenation zone effluent stream into an alkylation zone operated at alkylation conditions to produce an alkylation zone effluent stream which comprises isobutane, normal butane and $C_8$ hydrocarbons;
   (e) passing the alkylation zone effluent stream into the fractionation zone comprising said one column of step (a);
   (f) removing a third process stream, which is rich in isobutane, from the fractionation zone and passing at least a portion of the third process stream into the alkylation zone;
   (g) removing a fourth process stream, which comprises propane and isobutane, from the fractionation zone and passing substantially all the hydrocarbons present in the fourth process stream into a depropanizer column;
   (h) removing an isobutane-rich fifth process stream from the depropanizer column and passing the fifth process stream into the butane dehydrogenation zone as at least a portion of said second process stream; and,
   (i) removing a net product stream comprising saturated $C_8$ hydrocarbons from the fractionation zone of step (a).

2. The process of claim 1 further characterized in that a portion of the third process stream is passed into the butane dehydrogenation zone.

3. The process of claim 2 further characterized in that the division of the third process stream into a portion which is passed into the alkylation zone and a portion which is passed into the butane dehydrogenation zone is based on a measurement representative of the isobutane inventory in the process.

4. The process of claim 3 further characterized in that a measurement representative of the isobutane inventory of the process is obtained by passing the third process stream into a surge vessel and monitoring the liquid level within the surge vessel.

5. The process of claim 4 further characterized in that the size of the portion of the third process stream which is passed into the butane dehydrogenation zone is increased if the liquid level in said surge drum rises above a predetermined setpoint.

6. The process of claim 5 further characterized in that a portion of the third process stream is admixed with the fifth process stream to form said second process stream.

7. The process of claim 1 further characterized in that a sixth process stream which comprises $C_5$-plus hydrocarbons is removed from the butane isomerization zone and passed into the fractionation zone.

8. The process of claim 1 further characterized in that the fractionation zone comprises a single fractionation column.

9. A hydrocarbon conversion process which comprises the steps of:
   (a) passing a feed stream which comprises a mixture of isobutane and normal butane into a fractionation zone comprising one fractionation column;

(b) removing a first process stream, which is rich in normal butane, from the fractionation zone and passing the first process stream into a butane isomerization zone operated at isomerization conditions to produce a butane isomerization effluent stream which comprises isobutane and normal butane;

(c) passing the butane isomerization zone effluent stream and a hereinafter characterized second process stream into a butane dehydrogenation zone operated at dehydrogenation conditions to produce a dehydrogenation zone effluent stream which comprises isobutane, normal butane, isobutylene, butene-1 and butene-2;

(d) passing the butane dehydrogenation zone effluent stream into an alkylation zone operated at alkylation conditions to produce an alkylation zone effluent stream which comprises isobutane, normal butane and $C_8$ branched chain hydrocarbons;

(e) passing the alkylation zone effluent stream into the fractionation zone comprising said one column of step (a);

(f) removing a third process stream, which is rich in isobutane, from the fractionation zone, passing a first portion of the third process stream into the alkylation zone and passing a second portion of the third process stream into the butane dehydrogenation zone as at least a portion of said second process stream; and (g) removing a net product stream comprising $C_8$ branched chain hydrocarbons from the fractionation zone of step (a).

10. The process of claim 9 further characterized in that the division of the third process stream into said first and second portions is regulated by measuring a value representative of the isobutane inventory of the equipment used in performing the process and adjusting the rate of flow of said first and second portions as required to reduce any difference between the measured value and a predetermined setpoint.

11. The process of claim 10 further characterized in that the third process stream is passed through a liquid surge vessel and in that the liquid height within this surge vessel is the measured value used in adjusting the rate of flow of said first and second portions of the third process stream.

12. The process of claim 10 further characterized by the following steps:
(i) removing a fourth process stream, which comprises propane and isobutane, from the fractionation zone and passing at least the majority of the hydrocarbons present in the fourth process stream into a depropanizer column; and
(ii) removing an isobutane-rich fifth process stream from the depropanizer column and passing the fifth process stream into the butane dehydrogenation zone.

13. The process of claim 11 further characterized in that a sixth process stream which comprises $C_5$-plus hydrocarbons is removed from the butane isomerization zone and passed into the fractionation zone.

14. The process of claim 13 further characterized in that liquid phase hydrofluoric acid is employed as an alkylation catalyst within the alkylation zone.

* * * * *